United States Patent [19]

Kondo et al.

[11] Patent Number: 4,647,695

[45] Date of Patent: Mar. 3, 1987

[54] METHOD OF PREPARING TRIFLUOROACETIC ACID FROM TRICHLOROTRIFLUOROETHANE

[75] Inventors: Takeshi Kondo; Masamichi Maruta, both of Kawagoe; Hideki Oshio, Omiya, all of Japan

[73] Assignee: Central Glass Company, Limited, Ube, Japan

[21] Appl. No.: 713,687

[22] Filed: Mar. 19, 1985

[30] Foreign Application Priority Data

Mar. 21, 1984 [JP] Japan ................... 59-52192

[51] Int. Cl.[4] ........................................... C07C 51/093
[52] U.S. Cl. .................................................. 562/605
[58] Field of Search ............. 562/602, 604, 605; 560/222; 260/544 Y

[56] References Cited

U.S. PATENT DOCUMENTS

| | | | |
|---|---|---|---|
| 1,870,601 | 8/1932 | Britton et al. | 260/544 Y |
| 2,396,076 | 3/1946 | Benning et al. | 562/605 |
| 3,151,051 | 9/1964 | Braid et al. | 562/605 |
| 3,288,850 | 11/1966 | Nychka et al. | 52/605 |
| 4,172,957 | 10/1979 | Carreia et al. | 562/604 |
| 4,340,548 | 7/1982 | Anello et al. | 562/605 |

FOREIGN PATENT DOCUMENTS

| | | | |
|---|---|---|---|
| 2947376 | 6/1981 | Fed. Rep. of Germany | 562/605 |
| 58-159440 | 9/1983 | Japan | 562/605 |

OTHER PUBLICATIONS

J. Chem. Soc., 1959, "Oxidation of Polyhologen-compounds, Part II", pp. 387 to 396.

*Primary Examiner*—James H. Reamer
*Attorney, Agent, or Firm*—Fleit, Jacobson, Cohn & Price

[57] ABSTRACT

Trifluoroacetic acid is easily formed by hydrolysis of 1,1,1-trichloro-2,2,2-trifluoroethane with water in the presence of a catalyst comprising an inorganic metal compound, preferably a chloride of Mn, Fe, Co, Ni, Cu or Zn. Preferably the hydrolysis reaction is carried out as a vapor phase contact reaction at 200°–400° C., using 5–15 moles of water per mole of trichlorotrifluoroethane.

3 Claims, No Drawings

METHOD OF PREPARING TRIFLUOROACETIC ACID FROM TRICHLOROTRIFLUOROETHANE

BACKGROUND OF THE INVENTION

This invention relates to a method of preparing trifluoroacetic acid, or trifluoroacetyl chloride if desired, from 1,1,1-trichloro-2,2,2-trifluoroethane.

Trifluoroacetic acid is useful as an intermediate material for some medicines and agricultural chemicals. For industrial preparation of this compound, 1,1,1-trichloro-2,2,2-trifluoroethane is one of the hitherto chosen starting compounds.

It is well known that trifluoroacetic acid is formed by the reaction of 1,1,1-trichloro-2,2,2-trifluoroethane with fuming sulfuric acid or anhydrous sulfuric acid in the presence of a suitable catalyst such as mercury sulfate, boron trifluoride (West German patent specification No. 2,947,376) or bromine (U.S. Pat. No. 4,340,548). However, disadvantages of this method reside in that the reactant acid is inconvenient for handling and that the post-reaction treatment of the waste acid is troublesome.

Also it is known that trifluoroacetic acid can be formed by a photochemical reaction of 1,1,1-trichloro-2,2,2-trifluoroethane in the presence of chlorine and water (J. Chem. Soc., 1959, 387). However, this method is not favorable for industrial practice because the reaction gives a small amount of hydrofluoric acid, which causes devitrification of glass used in the light source part of the reaction apparatus in a relatively short period of time, and also because the selectivity of the reaction to trifluoroacetic acid is not satisfactorily high.

SUMMARY OF THE INVENTION

It is an object of the present invention to provide a novel method of easily and efficiently preparing trifluoroacetic acid from 1,1,1-trichloro-2,2,2-trifluoroethane.

A method according to the invention for the preparation of trifluoroacetic acid is characterized by hydrolyzing 1,1,1-trichloro-2,2,2-trifluoroethane by its reaction with water in the presence of a catalyst which comprises an inorganic metal compound.

It is suitable to carry out this hydrolysis reaction as a vapor phase reaction at a temperature above about 200° C. Preferably, a chloride of manganese, iron, cobalt, nickel, copper or zinc is used as the metal compound of the catalyst.

Although 1,1,1,-trichloro-2,2,2-trifluoroethane is known as a compound very low in reactivities, we have unexpectedly found that this compound is readily hydrolyzed by water in the presence of a certain metal compound and that in this hydrolysis reaction the selectivity to trifluoroacetic acid is very high. In general it is known that hydrolysis of a compound having —CCl$_3$ group as a terminal group can be achieved relatively easily by using a suitably concentrated sulfuric acid. However, it is also known that the hydrolysis of such a compound becomes difficult when the compound has a fluorine atom adjacent to the terminal —CCl$_3$ group, and becomes utterly impossible when the adjacent position is saturated with fluorine atoms. We have found no report on the hydrolysis of 1,1,1-trichloro-2,2,2-trifluoroethane by its simple reaction with water.

The method according to the invention can readily be put into industrial practice, and is advantageous in the ease of operations, lowness of the material cost and good yield of trifluoroacetic acid. If desired, it is also possible to obtain trifluoroacetyl chloride by this method as an intermediate of trifluoroacetic acid.

DESCRIPTION OF THE PREFERRED EMBODIMENTS

As regards the catalyst used in the present invention, an effective metal compound can be chosen among chlorides and sulfates of Mn, Fe, Co, Ni, Cu and Zn. Besides, oxides of these metals are also usable because the hydrolysis reaction according to the invention gives a relatively large amount of hydrogen chloride which acts on a metal oxide catalyst present in the reaction system to convert the oxide into chloride. Chlorides of the above named metals are preferred to the sulfates and oxides, and ferric chloride is evaluated as to be the best catalytic metal compound for use in this invention in respect of both activity and selectivity.

To enhance catalytic activity, preferably the selected metal compound is used in the form of a deposit on a porous carrier. The material of the carrier is not particularly limited and may be chosen among the commonly used porous carrier materials, such as active carbon, alumina and silica for example.

Considering the effect on the activity of the catalyst, it is suitable to carry out the reaction at a relatively high temperature. More particularly, a preferable range of the reaction temperature is from about 200° C. to about 400° C.

The starting material, 1,1,1-trichloro-2,2,2-trifluoroethane (hereinafter, called trichlorotrifluoroethane for simplicity) has a boiling point of 45.7° C. Even when a reaction temperature in the above-mentioned range is employed it is possible to carry out the reaction as a liquid phase reaction under superatmospheric pressure conditions, but this is rather troublesome and incurs an increase in the cost of equipment. Furthermore, corrosive action of by-produced hydrogen chloride on the apparatus becomes more significant in liquid phase. Therefore, it is advantageous to carry out the reaction as a vapor phase reaction.

In the case of vapor phase reaction, the method of the invention is embodied in a continuous contact reaction process using a fixed bed of a selected metal compound catalyst. The catalyst bed is kept heated at a temperature in the range from 200° to 400° C., and more preferably from 250° to 350° C. Water and trichlorotrifluoroethane are fed to a preheating zone of the reaction apparatus at suitably proportioned flow rates by means of metering pumps to thereby prepare a mixed vapor of the reactants. The mixed vapor is continuously passed through the heated catalyst bed, where the intended hydrolysis reaction takes place. To form trifluoroacetic acid, the stoichiometric mole ratio of water to trichlorotrifluoroethane is 2:1. In practice it is necessary to use a larger amount of water, but it is undesirable to use an excessively large amount of water because the reaction product becomes a relatively low concentration solution of trifluoroacetic acid in hydrochloric acid. Usually it is suitable to use 5 to 15 moles of water per mole of trichlorotrifluoroethane. It is suitable that the gas hourly space velocity (G.H.S.V.) of the mixed vapor passing through the catalyst bed falls in the range from 100 to 500 hr$^{-1}$. The contact time may be adjusted to a few seconds at the shortest and to about one minute at the longest. Usually it suffices to ensure a contact time of 2-20 sec.

The reaction product in vapor phase is cooled to condense into an aqueous mixed solution of trifluoroacetic acid and by-produced hydrogen chloride. Trifluoroacetic acid is separated from this solution by distillation. Where the reaction product contains a substantial amount of unreacted trichlorotrifluoroethane, the liquid obtained by condensation divides into two layers and, therefore, can easily be separated into a solution of trifluoroacetic acid and unreacted trichlorotrifluoroethane which can be reused in the above-described hydrolysis reaction.

The invention will further be illustrated by the following nonlimitative examples.

EXAMPLE 1

A granular catalyst was prepared by leaving about 2–5 mm grains of active carbon immersed in 40 wt % aqueous solution of ferric chloride for about 12 hr at room temperature and then drying the treated active carbon grains in air at 80° C. for 3 hr. A fixed catalyst bed was prepared by packing 120 ml of this ferric chloride on active carbon catalyst.

The catalyst bed was kept heated at 290° C. Using metering pumps, 0.23 g/min of water and 0.20 g/min of trichlorotrifluoroethane were continuously fed to the heated catalyst bed through a preheating zone. That is, the mole ratio of water to trichlorotrifluoroethane brought into reaction was about 12:1. A vapor flowed out of the catalyst bed was passed through a cooled pipe to collect a liquid phase product in a container. The operation was continued until the feed of trichlorotrifluoroethane reached 88 g.

The collected product was analyzed by gas chromatography and $^{19}F$ NMR to reveal that 39.3 g of trifluoroacetic acid was formed and that 15 g of unreacted trichlorotrifluoroethane was present. Therefore, the conversion of trichlorotrifluoroethane was 83.0%, and the selectivity of the hydrolysis reaction to trifluoroacetic acid was calculated to have been 88.5%.

EXAMPLES 2–7

In these examples, vapor phase contact reaction between water and trichlorotrifluoroethane was carried out generally in the manner as described in Example 1 under different reaction conditions as shown in the following table. In Examples 4–7, $CuCl_2$, $MnCl_2$ or $ZnCl_2$ was used as the catalytic metal compound 10 in place of $FeCl_3$ in Examples 1–3. In every case the metal chloride was in the form of a deposit on the granular active carbon mentioned in Example 1. In these examples the percent conversion of trichlorotrifluoroethane and the selectivity of the hydrolysis reaction to trifluoroacetic acid varied as shown in the same table.

| | Catalyst | Reaction Temp. (°C.) | G.H.S.V. $(hr^{-1})$ | Mole Ratio $\frac{H_2O}{CCl_3CF_3}$ | Conversion of $CCl_3CF_3$ (%) | Selectivity to $CF_3COOH$ (%) |
|---|---|---|---|---|---|---|
| Ex. 2 | $FeCl_3$ | 270 | 112 | 8.1:1 | 30.2 | 91.0 |
| Ex. 3 | $FeCl_3$ | 280 | 132 | 8.0:1 | 54.4 | 89.4 |
| Ex. 4 | $CuCl_2$ | 270 | 152 | 9.7:1 | 33.6 | 89.1 |
| Ex. 5 | $CuCl_2$ | 280 | 147 | 10.0:1 | 39.9 | 65.8 |
| Ex. 6 | $MnCl_2$ | 280 | 130 | 9.2:1 | 20.2 | 83.2 |
| Ex. 7 | $ZnCl_2$ | 270 | 146 | 6.7:1 | 38.6 | 87.6 |

EXAMPLE 3A

In Example 3, unreacted trichlorotrifluoroethane was separated and recovered from the reaction product. The recovered trichlorotrifluoroethane was reused in the above-described vapor phase contact reaction with water under the same reaction conditions as in Example 3. In this case the conversion of trichlorotrifluoroethane was 55.7%, and the selectivity of the hydrolysis reaction to trifluoroacetic acid was 88.6%. These values can be taken to be practically in agreement with the values in Example 3. This example demonstrates that in the method according to the invention loss of the starting material can be minimized by recycling the unreacted material which can easily be separated from the reaction product.

What is claimed is:

1. A method of preparing trifluoroacetic acid, comprising the step of hydrolyzing 1,1,1-trichloro-2,2,2-trifluoroethane by its vapor phase contact reaction with water at a temperature in the range from about 200° C. to about 400° C. in the presence of a catalyst which consists essentially of a porous active carbon and a metal chloride deposited on said active carbon, said metal being selected from the group consisting of Mn, Fe, Co, Ni, Cu and Zn.

2. A method according to claim 1, wherein said metal compound is ferric chloride.

3. A method according to claim 1, wherein the mole ratio of said water to said 1,1,1-trichloro-2,2,2-trifluoroethane is in the range from 5:1 to 15:1.

* * * * *